United States Patent [19]

Guo et al.

[11] Patent Number: 5,363,050
[45] Date of Patent: Nov. 8, 1994

[54] QUANTITATIVE DIELECTRIC IMAGING SYSTEM

[76] Inventors: Wendy W. Guo; Theodore C. Guo, both of 10618 Tanager La., Potomac, Md. 20854

[21] Appl. No.: 576,209

[22] Filed: Aug. 31, 1990

[51] Int. Cl.$^5$ ............................................. G01N 29/00
[52] U.S. Cl. .................................... 324/638; 324/642; 324/644; 73/602; 73/620; 128/653.2; 364/481
[58] Field of Search ............... 324/638, 642, 644, 629, 324/632, 631; 73/602, 619, 620; 128/653 R; 364/481, 482

[56] References Cited

U.S. PATENT DOCUMENTS

| | | | |
|---|---|---|---|
| 4,135,131 | 1/1979 | Larsen et al. | 324/58.5 A |
| 4,162,500 | 7/1979 | Jacobi et al. | 343/772 |
| 4,247,815 | 1/1981 | Larsen et al. | 324/58.5 A |
| 4,271,389 | 6/1981 | Jacobi et al. | 324/58.5 A |
| 4,552,151 | 11/1985 | Bolomey et al. | 128/653 |
| 5,253,530 | 10/1993 | Letcher, III | 73/602 |

OTHER PUBLICATIONS

"Computation of Electromagnetic Wave Scattering From An Arbitrary Three-Dimensional Inhomogeneous Dielectric Object", Reprint from IEEE Transactions on Magnetics MAG-25, Jul. 1989.
"Physics of image formation by microwave scattering", Proceedings of the SPIE-The International Society for Optical Engineering, vol. 767, Medical Imaging 1-6, Feb. 1987, New Port Beach, Calif.
"Scattering of Vector Waves by Arbitrary Three-Dimensional Dielectric Objects", Proceedings of the 1987 International Microwave Symposium, IEEE Publication 87TH0183-4, Feb. 1987.
"Medical Applications of Microwave Imaging", edited by Lawrence E. Larsen, et al., IEEE Press, Jan. 1986, pp. 167-183, 126-128, 143-163.
"A Local Field Study of a Water-Immersed Microwave Antenna Array for Medical Imagery and Therapy", T. C. Guo, et al., IEEE Transactions on Microwave Theory and Techniques, vol. MTT-32, No. 8, Aug. 1984.
"Frontiers of Engineering and Computing in Health Care-1984", Proceedings-Sixth Annual IEEE Engineering in Medicine and Biology Society, Los Angeles Hilton Hotel, Los Angeles, Calif., 15-17, Sep. 1984, edited by John L. Semmlow and Walter Welkowitz, pp. 532-539.
"Medical Microwave Imagery: An Inverse Scattering Approach", IEEE Conference Digest of the Eighth International Conference on Infrared and Millimeter Waves, Jan. 1983, by T. C. Guo.
Guo et al, "Non Invasive Dielectric Evaluation by Scanning Microwave Frequency or Incident Direction" (Sep. 1989).
Guo et al, "Dielectric Imaging by Microwave Inverse Scattering and a Technique to Stabilize Matrix Inversion" (Sep. 1989).
Guo et al, "Three Dimensional Dielectric Imaging by Microwave Inverse Scattering with Resolution Unlimited by Wavelength"(Oct. 1989).

*Primary Examiner*—Kenneth A. Wieder
*Assistant Examiner*—Glenn W. Brown
*Attorney, Agent, or Firm*—Leydig, Voit & Mayer

[57] ABSTRACT

In a microwave imaging system, a three dimensional profile of the dielectric permittivity of a target is obtained. A transmitter transmits microwaves toward a target, and the target scatters the microwaves. The scattered waves are received by an antenna and are converted into suitable data for application to a digital computer. The computer processes the data using either a scattering matrix algorithm or a Fourier transform algorithm. The computer then generates data representative of a three dimensional profile of dielectric permittivity which can be displayed on a suitable display device such as a CRT.

15 Claims, 4 Drawing Sheets

QUANTITATIVE DIELECTRIC IMAGING SYSTEM

FIELD OF THE INVENTION

The present invention relates generally to non-destructive testing and evaluation systems, and more specifically, the invention relates to a three dimensional quantitative dielectric imaging system.

BACKGROUND OF THE INVENTION

All non-destructive testing and evaluation (NDT&E) techniques utilize some sort of probing radiation and characterize the target by measuring the scattered, reflected, or attenuated radiation. X-ray tomography and CAT scan image a target by measuring its X-ray attenuation. Sonogram maps a target by scanning the reflection of ultrasonic radiation from different layers of the target. Nuclear magnetic resonance (NMR) produces detailed pictures of a target with respect to the relaxation time of its molecules' magnetic moment. Neutron scattering is used to detect content of some atomic elements in the material. Since different radiation interacts with the target through different physical mechanism, the image thereby obtained represents only the image of the target with respect to the particular physical property that is responsible for such interaction. Among these existing NDT&E techniques, there is a missing gap of imaging that provides dielectric data in the RF to microwave regime. Since there is a vast data resource on dielectric permittivity of various materials and its temperature and pressure dependencies, dielectric imaging offers a valuable means to evaluate material, temperature, and pressure profiles of a composite object or a complex system. Dielectric permittivity of new materials can easily be measured by a network analyzer, which is commercially available, and added to the data bank for image evaluation.

The present invention relates to a three-dimensional quantitative dielectric image technology by microwave inverse scattering. There are many advantages of using the present invention over other conventional techniques. The present invention offers three-dimensional dual images of real and imaginary parts of dielectric permittivity while X-ray gives only a two-dimensional picture of attenuating power along the radiation path; though CAT scan by X-ray provides three-dimensional images of the targets' density in terms of X-ray absorption per unit volume, each three-dimensional image requires a large number of X-ray exposures. A neutron scattering device requires a radioactive source, whereas the present invention employs low level non-ionizing radiation. Although a microwave imaging system may not provide as good an image resolution as that of NMR, it provides a three-dimensional profile of dielectric permittivity, which is more sensitive for differentiating materials. Another advantage of the present invention is its transportability and low cost, which is believed to be much lower than that of either a NMR or a CAT scan system. The operating cost of the present invention is also orders of magnitude lower than that of NMR or CAT systems. As to sonogram, it is essentially an echogram, in the sense that it detects only discontinuities in the elastic properties of the target. In many applications, imaging in accordance with the present invention may be complementary to sonograms, because the present invention provides a dielectric image whereas sonogram yields an elastic image. Microwave systems do have limitations. Such systems cannot penetrate materials with high electric conductivity; for a metallic object, it can only image its surface shape or, in some cases, the conductivity profile of its surface.

The conventional concept of imaging by microwave scattering is quite similar to the way one perceives an object by seeing. Light waves are scattered from an object and the scattered waves are then received by nerve endings in the retina of the eyes. The detected signals are relayed to the brain, which then processes the signals and constructs an image, resulting in the way one perceives the object. One cannot see the interior of an object because light dissipates rapidly in most objects and no light is scattered from the interior of the object. Since microwave penetrates rather deeply through most dielectric materials, it can be scattered by the interior of most dielectric objects and propagate to the outside. In accordance with the present invention, data from the scattering measurement may then be processed to construct a three-dimensional image of the object. Even for objects that are highly microwave absorbing, such as a biological target, it has been demonstrated from conventional techniques that a specific absorption rate (SAR) in the order of microwatt per gram to tens of microwatt per gram yields a scattered signal that is sufficient for dielectric image reconstruction.

Some of the above-mentioned imaging techniques produce quantitative images, but most give only qualitative images. The difference between a qualitative image and a quantitative image is analogous to that between "seeing" and "measuring". While "seeing" an object provides useful information, it is more desirable to be able to "measure" the object so that the result can be compared to known experimental data. This is particularly useful for medical diagnosis for the purpose of detecting and discriminating abnormal from normal tissues in advance of biopsy. There is a rich data resource concerning the dielectric permittivity of biological tissues. A three-dimensional profile of dielectric permittivity of a part of a patient's body will furnish a rich resource of diagnostic information. Dielectric dependence on other physical quantities, such as temperature and pressure, also may provide a non-invasive means for measuring these quantities.

Though biological subjects are highly absorbing to microwaves, it has been demonstrated that the scattered microwave provides enough signal for dielectric image reconstruction. Indeed, a two dimensional microwave dielectric image of a canine kidney immersed in a cylindrical water tank of about 30 inches diameter has been produced in the past. L. E. Larsen, et al., "Microwave Imaging Systems for Medical Diagnostic Applications", 6th Annual Conference IEES Engr. in Medicine and Biology Soc., Los Angeles, September 1984. The results demonstrated that penetration depth was not a problem.

In addition to medical applications there is also a need for improved imaging in the non-destructive testing and evaluation of structures such as buildings and bridges and in measuring multiphase flows in power plants. A three dimensional profile of the dielectric permittivity of such objects can provide useful data that is not available with conventional techniques.

The ubiquitous presence of multiphase flows in vital industrial areas of contemporary society, such as conventional and nuclear power generation, is well known. Just as well known is the substantial problems that such flows pose to the design engineer in view of the rudimentary degree with which their behavior is currently understood. Of particular concern is the behavior of multiphase flows in unsteady situations such as may arise in operational transients or, more dangerously, under accident conditions. In many cases, it is difficult to predict even such basic parameters as pressure drop, mean phase content (e.g., void fraction), global heat transfer coefficients, and so forth. In such cases measurement is the only possible approach and a large number of techniques have been devised, tested, and developed for this purpose. The difficulty of the task is underscored by the very large number of papers devoted to this aspect alone of multiphase flow research. But even experiments cannot fully simulate such situations as very rapid transients or large-scale systems, for which the development of theoretical approaches is imperative. However, any modelling effort of practical engineering significance can only be achieved sacrificing the overwhelming amount of information that the accurate description of such flows would require. The averaged equations used for this purpose are therefore, by their very nature, incomplete and do not give rise to a mathematically closed problem.

Microwave imaging addresses simultaneously some of the most important and basic aspects of multiphase flow experimentation, the measurement of void fraction, of the interfacial area, and of the flow topography. The application of the present invention to multiphase flows from its non-intrusiveness, real-time capability, ease of application, and reliability. The present invention provides quantitative dielectric imaging based on inverse scattering of microwaves from the multiphase mixture. In this sense it represents an approach intermediate between the low-frequency impedance gauges and the high-energy radiation scattering techniques that have both been in use for some time. Contrary to these techniques, however, the use of microwave frequencies enables the information contained in the wave-vector and frequency spaces to be fully exploited. The final result is a much more detailed measurement, to a large extent free of the many problems and ambiguities that plague conventional approaches.

A number of experimental techniques rely on the interaction between the multiphase flow and electromagnetic radiation. At the low-frequency end, impedance gauges that operate at kHz or MHz frequencies are limited in their spatial resolution by the "effectively dc" field that they use. At the other extremum of X and gamma rays, the wavelength is so short that no information from wave-number space can be extracted from the signal. The need for the use of microwave frequencies, therefore, becomes very attractive in analyzing multiphase flows.

Accordingly, there is a need for a three dimensional microwave imaging system that can be used in medical application and other non-destructive testing and evaluation uses such as the imaging of structures and multiphase flows, and interrogation of luggages.

SUMMARY OF THE INVENTION

The present invention relates to a microwave imaging system that can obtain a three dimensional dielectric permittivity profile of a target from microwaves scattered from the target.

In a first embodiment of the present invention a target is disposed in front of a microwave transmitter, and the target is surrounded by an antenna formed from a plurality of coaxial cables. Microwave energy directed at the target by the transmitter is scattered by the target and received by the antenna. The scatter data received by the antenna is processed by a general purpose digital computer using a scattering matrix algorithm, to provide a three dimensional profile of the dielectric permittivity of the target. The dielectric permittivity data can then be displayed.

In the second embodiment of the present invention, the microwaves scattered by the target are received by an antenna disposed at a greater distance from the target than in the first embodiment. The scatter data is processed by a general purpose computer, using a Fourier transform algorithm, to provide a three dimensional profile of dielectric permittivity of the target. The permittivity data then can be displayed on a suitable display device.

DETAILED DESCRIPTION OF THE INVENTION

Wavelength places a limit on resolution only when some far-field approximation is used for the scattering field. A common approach to electromagnetic scattering in a far-field is to make a first order approximation, which reduces the scattering pattern to a fourier transform of the source. Then one may retrieve the source information by inverting the Fourier transform of the scattering pattern. However, neglecting higher order terms also throws away much information about the target. Thus, the conventional inverse Fourier transform yields only a two-dimensional projection of the source profile, and the resolution is limited to the wavelength of the probing radiation. To overcome the wavelength limitation and to retrieve all three dimensions of the source profile, one has to invert the scattering field without making first order approximation. In the present invention, the integral equation for the scattering wave is converted into a scattering matrix form, then an algorithm to invert the scattering matrix is used. In order to stabilize the matrix inversion, scattering matrix in the near zone is employed. The idea is somewhat related to the electrostatic case where a number of unknown point charges distributed in some fixed positions may be solved by measuring the electrostatic potentials at an equal number of points and inverting the set of algebraic field equations. As electrostatic field is equivalent to electrodynamic field with infinite wavelength, this illustrates the possibility of imaging by inverse scattering that yields a resolution unlimited by the wavelength. Though the scattering matrix is non-singular, it could be near singular if high resolution is demanded. Thus, for a target divided into a large number of small cells, the inversion of the scattering matrix may be unstable and thereby sensitive to noise. There are three possible approaches to enhancing stability. The first approach is to reduce symmetry of the scattering matrix through geometric configuration of target cells and observation points. The second approach is to use a dissipative dielectric as a background medium. The third approach is to increase the number of observation points to more than the number of cells in the target, so that there will be more equations than unknowns. Then a least-mean-square singular value decomposition (SVD) technique is used to fit all equations. The third approach is consistently effective in stabilizing the scattering inversion as hereinafter explained. Also, for most two-phase systems with water as liquid, the second approach is automatically in place since water is highly dissipative for microwaves.

Based on the Maxwell's theory, if the field is known everywhere in space, the source can be solved simply by differentiation. In an inverse scattering problem, scattering fields can be measured only in a limited region in space outside of the scatterer. The source-field relationship is complicated by the fact that the source of the scattering field is an explicit function of not only the dielectric permittivity of the scatterer, but also the field inside the scatterer, which is an implicit function of the scatterer. Furthermore, the source-field relationship is an integral equation. The problem of inverse scattering is to untangle the implicit relationship between the scatterer's dielectric permittivity and the field inside the scatterer. It should be noted that the term "scattering field" differs from the conventional definition in the sense that it refers to a field anywhere outside of the target; it does not need to be far away from the target. Indeed, the fields for image reconstruction must be close to the target in order to contain information on the depth of the target. In the present invention, the inverse scattering problem encompasses four steps: 1) developing an inverse scattering formulation to obtain the target's dielectric permittivity in terms of scattering field outside the target and incident field, 2) converting the integral formulation into a scattering matrix form, 3) devising an algorithm to invert the scattering matrix, and 4) stabilizing the inversion of the scattering matrix by a singular value decomposition technique.

A plane microwave is incident upon a scatterer to be imaged, and scattering fields are measured within a region outside the scatterer. It can be denoted by $V_o$ the region occupied by the scatterer, and by $V$ the region where scattering fields are measured. Let $\epsilon(X)$ denote, respectively, the dielectric permittivity of the background medium and that of the scatterer. Thus the quantity $\epsilon(X) - \epsilon_m$ vanishes outside $V_o$. The Maxwell's equations of the system may be written in the form: $M|f> = 0$, where $M$ represents the Maxwell's differential operators and $f$ the field quantities. The total field may be expressed as the sum of the scattering field and the incident field: $f = f^{(s)} + f^{(i)}$. The operator $M$ can be separated into two parts: $M = M_m - S$, with $M_m$ representing the Maxwell's operator in a homogenous background and $-S$ the operator due to the excess dielectric permittivity, $\epsilon(X) - \epsilon_m$. Then the Maxwell's equation may be written as $M_m|f^{(i)}> + M_m|f^{(s)}> = S|f>$. Since $M_m|f^{(i)}> = 0$, the equation becomes: $M_m|f^{(s)}> = S|f>$. Denote by $G_m$ the inverse of $M_m$; in the x-representation, $G_m(x,x')$ is the well known Green's function. Operating both sides by $G_m$, one then gets:

$$|f^{(s)}> = G_m S |f>. \tag{1}$$

Thus, the scattering problem has been reduced to a source-field problem in homogenous medium, with the source being $S|f>$. However, the source term still depends on the field inside the scatterer, which again depends on the scatterer $S$. The next step is to separate $S$, the dielectric permittivity of the scatterer, from the field inside $V_o$, and to express $S$ in terms of measurable quantities or a priori quantities, such as the scattering field $f^{(s)}$ inside $V$ or the incident field $f^{(i)}$ anywhere. First we note that eq. 1 defines only the product $G_m S$. So, given a pair $(G_m,S)$, one may re-factorize it to another pair $(G_m',S')$ such that $G_m'S' = G_m S$. The expressions of $G_m S$ are derivable from the Maxwell's equations. They depend on the choice of $|f>$, which may be the electric field $|E>$ or any other field quantity. We shall employ $|E>$ as the field $|f>$, derive the operators $M_m'$, $S'$, and $G_m' = M_m'^{-1}$ then re-factorize $G_m'S'$ to $G_m S$ such that the pair $(G_m,S)$ may facilitate the separation of the field from the source. Thus, from the Maxwell's equations, we first derive, in the Gaussian system of electromagnetic unit, $$M_m' = [\nabla^2 + k_m^2]\overleftrightarrow{I} \tag{2}$$

$$S'(x, x') = -[\nabla\nabla \cdot + k_m^2 \cdot \overleftrightarrow{I}] \frac{\epsilon(x) - \epsilon_m}{\epsilon_m} \cdot \delta(x - x') \tag{3}$$

From eq. 2 one obtains the x-representation of the inverse of $M_m'$:

$$G_m'(x, x') = -\frac{1}{4\pi} \frac{\exp(ik_m|x - x'|)}{|x - x'|} \cdot I \tag{4}$$

Since $[\nabla\nabla \cdot + k_m^2 \overleftrightarrow{I}]$ commutes with $M_m'$, it commutes with its inverse, $G_m'$. Therefore, from eq. 3, $G_m'S' = [\nabla\nabla \cdot + k_m^2 \overleftrightarrow{I}]G_m' \cdot [-(\epsilon - \epsilon_m)/\epsilon_m]$. Defining $G_m$ as $[\nabla\nabla \cdot + k_m^2 \overleftrightarrow{I}]G_m'$, we may refactorize $G_m'S'$ to the product of the following pair of $(G_m,S)$:

$$G_m(x, x') = -\frac{1}{4\pi} [\nabla\nabla \cdot + k_m^2 \cdot \overleftrightarrow{I}] \frac{\exp(ik_m|x - x'|)}{|x - x'|} \tag{5}$$

$$S(x, x') = -\frac{1}{\epsilon_m} [\epsilon(x) - \epsilon_m] \delta(x - x') \cdot I \tag{6}$$

The operator $S$ vanishes outside the scatterer and is diagonal in the sense that $S(x,x') = S(x)\delta(x - x')$. The diagonal elements of $S$ are exactly the negative of the fractional variations of scatterer's dielectric permittivity with respect to the background medium.

We shall now show that the form of $S$ given above enables us to separate the field from the source on the right-hand side of eq. 1. Since we are only concerned in the regions $V_o$ (the scatterer) and $V$ (the measuring region), we shall project all operators and fields onto these two regions. We shall use x to denote the point in $V$, and y a point in $V_o$. We shall also denote by $f$ and $f_o$, respectively, the projection of a field onto $V$ and $V_o$. Similarly, we denote by $G$ the projection of $G_m$ onto $V$ on the left and onto $V_o$ on the right (short-handed as $VG_m V_o$), and by $G_o$ the projection of $G_m$ onto $V_o$ from both sides ($V_o G_m V_o$). Thus, in the integral form, $G$ is $G(x,y')$, $G^{-1}$ is $G^{-1}(y,x')$, and $G_o$ is $G_o(y,y')$. With the above notation, eq. 1 then decomposes into $V$ part and $V_o$ part:

$$|f^{(s)}> = GS |f_o>. \tag{7}$$

$$|f_o^{(s)}> = G_o S |f_o>. \tag{8}$$

where we have utilized the equality $S|f> = S|f_o>$, which is due to the fact that $S$ vanishes outside $V_o$ and so it projects any field onto $V_o$. From eq. 7, $G^{-1}|f^{(s)}\rangle = S|f_o\rangle = S[|f_o^{(i)}\rangle + |f_o^{(s)}\rangle]$. Substituting eq. 8 for the second term inside the bracket, one gets $G^{-1}|f^{(s)}\rangle = S[|f_o^{(i)}\rangle + G_oS|f_o\rangle]$, where $S|f_o\rangle$ in the second term inside the bracket is, by eq. 7, $G^{-1}|f^{(s)}\rangle$. So this last equation gives:

$$S[|f_o^{(i)}\rangle + G_oG^{-1}|f^{(s)}\rangle] = G^{-1}|f^{(s)}\rangle \tag{9}$$

In the above equation, the first factor on the left-hand side represents the dielectric permittivity of the scatterer, and the rest are either measured quantity or a priori quantities. So we have succeeded in separating the field from the source. Since the $S(y,y') = S(y) \cdot \delta(y-y')$, $\langle y|S|f\rangle = S(y) \cdot f(y)$, so from eq. 9 one immediately obtains:

$$S(y) = \frac{-1}{\epsilon_m}[\epsilon(y) - \epsilon_m] = \frac{\langle y|G^{-1}|f^{(s)}\rangle}{\langle y|f_o^{(i)}\rangle + \langle y|G_oG^{-1}|f^{(s)}\rangle} \tag{10}$$

or, in the integral form, $$S(y) = \frac{-1}{\epsilon_m}[\epsilon(y) - \epsilon_m] = \frac{\iiint dx' G^{-1}(y, x')f^{(s)}(x')}{f_o^{(i)}(y) + \iiint_{V_o} dy' \iiint_V dx' G_o(y, y')G^{-1}(y', x')f^{(s)}(x')} \tag{11}$$

Equation 10 or 11 is the basic inverse scattering equation. They give the scatterer's dielectric permittivity in terms of the scattering field $f^{(s)}(x)$ inside the measuring region and the incident field $f_o^{(i)}(y)$ inside the scatterer. The rest of the problem is computational. We approach this by digitizing the operators $G_o$ and $G$, and converting the two operators into matrices.

Short of an analytic method to compute the integrals on the right hand side of the inverse formula, eq. 11, we shall digitize the formula and convert the integral operators to matrices. To this end, we divide $V_o$ into a number of small cells. Label the cells by $\tau_j$ and their centers by $y_j$. Each cell $\tau_j$ must be small enough that the field inside may be approximated by its value at $y_j$. This means that the dimension of the cells must be smaller than a fraction, say $\frac{1}{4}$ or smaller, of the electromagnetic wavelength inside the scatterer. Then integration over $V_o$ may be converted into summation of integrals over cells $\tau_j$ as below:

$$\iiint_{V_o} G(x, y')f_o(y')dy' \approx \sum_j \left[ \iiint_{y \in \tau_j \subset V_o} G(x, y')dy' \right] f_o(y_j) \tag{12}$$

Let $\{x_i\}$ represent the set of points where scattering fields are measured, and denote by $G_{ij}$ the integral side the bracket for $x = x_i$:

$$G_{ij} = \iiint_{y' \in \tau_j \subset V_o} G(x_i, y')dy' \tag{13}$$

where $G(x,y')$ is given by eq. 5. We shall refer to $G_{ij}$ as the Green's matrix. With the above definition, eq. 12 may be written in the matrix form:

$$\iiint_{V_o} G(x_i, y')f_o(y')dy' = \sum_j G_{ij}f_o(y_j) \tag{14}$$

The problem now is to find the matrix elements $G_{ij}$ as defined in eq. 13. By approximating the cell with a sphere of equal volume, the integral may be evaluated analytically. Denoting by $a$ the radius of the spherical cell, the matrix elements of the Green's matrices, $G_o$ and $G$ are:

$$(G_o)_{ii} = \overleftrightarrow{I}\left[1 + \frac{2}{3}a^2 \cdot \frac{d}{da}\left(-\frac{\exp(ik_m a)}{a}\right)\right] \tag{15}$$

$$(G_o)_{ij \, (i \neq j)} = a \cdot \frac{\exp(ik_m|y_i - y_j|)}{|y_i - y_j|} \cdot \tag{16}$$

$$\left[\cos(k_m a) - \frac{1}{k_m a}\sin(k_m a)\right] \cdot$$

$$\left[\overleftrightarrow{I}\left(1 - \frac{1}{ik_m|y_i - y_j|} + \frac{1}{(ik_m|y_i - y_j|)^2}\right) - \right.$$

$$\frac{y_i - y_j}{|y_i - y_j|}\frac{y_i - y_j}{|y_i - y_j|}\left(1 - \frac{3}{ik_m|y_i - y_j|} + \right.$$

$$\left.\left.\frac{3}{(ik_m|y_i - y_j|)^2}\right)\right]$$

$$(G)_{ij} = a \cdot \frac{\exp(ik_m|x_i - y_j|)}{|x_i - y_j|} \cdot \left[\cos(k_m a) - \frac{1}{k_m a}\sin(k_m a)\right] \cdot \tag{17}$$

$$\left[\overleftrightarrow{I}\left(1 - \frac{1}{ik_m|x_i - y_j|} + \frac{1}{(ik_m|x_i - y_j|)^2}\right) - \right.$$

$$\frac{x_i - y_j}{|x_i - y_j|}\frac{x_i - y_j}{|x_i - y_j|}\left(1 - \frac{3}{ik_m|x_i - y_j|} + \right.$$

$$\left.\left.\frac{3}{(ik_m|x_i - y_j|)^2}\right)\right]$$

Note that the off-diagonal matrix elements of $G_o$ and $G$ are of identical form; $(G_o)_{ij}$ may be obtained by replacing $x_i$ in $(G)_{ij}$ by $Y_i$. As to the S operator, eq. 6 gives:

$$S_{ij} = \frac{-1}{\epsilon_m}[\epsilon(y_i) - \epsilon_m]\delta_{ij} \cdot \overleftrightarrow{I}(y_i \subset V_o) \tag{18}$$

So S is diagonal with the diagonal element $S_{ii}$ being the negative of the fractional variation of the dielectric permittivity of the $i^{th}$ cell in the scatterer with respect to the background medium.

The Green's matrices depend only on the geometry of $V_o$ and $V$, and the geometrical arrangement of the cells inside them. They are independent of the scatterer S. The accuracy of the reexpressions in eqs. 15-17 has been tested and was found to be within 0.1% error for a one-cell scatterer with size equal to λ/5, where λ is the wavelength inside the scatterer, and within 4% error for a scatterer divided into 308 cells of size equal to λ/5. since the error increases with α/λ, it possibly is mainly due to the assumption that the field is constant inside each cell. Therefore, the accuracy may be greatly improved by removing the principal oscillatory factor from the field. This may be accomplished by incorporating the plane-wave factor, exp(ik·x), into $G^v$ and $G_o$ (viz., into the integral operator $G(x_i,y')$ in eq. 13), where k may be the average value or a test value of the wave vector in the scatterer. For a weak scatterer, one may simply incorporate the plane-wave factor of the incident wave, exp(ik$_m$·x), into $G_v$ and $G_o$. Otherwise, the value of the test k may be $k_m\sqrt{\epsilon}/\sqrt{\epsilon_m}$, where ε is an assumed average . value of dielectric permittivity of the scatterer.

Having digitized the integral operators G and $G_o$ into Green's matrices, eq. 11 may then be written in the following matrix form:

$$S_{ii} = \frac{-1}{\epsilon_m}[\epsilon(y_i) - \epsilon_m] = \frac{\sum_j (G^{-1})_{ij} f^{(s)}(x_j)}{f_o^{(i)}(y_i) + \sum_{j,k}(G_o)_{ij}(G^{-1})_{jk}f^{(s)}(x_k)} \quad (19)$$

This equation gives the dielectric permittivity $S_{ii}$ of the $i^{th}$ cell in the scatterer in terms of the scattering field $f^{(s)}(X_j)$ outside the scatterer, and the incident field $f_o^{(i)}(Y_i)$ inside the scatterer; the incident field is known analytically.

Equation 19 is the basis for developing an image reconstruction algorithm. By measuring the scattering field in any region outside the scatterer, the formula gives the scatterer's distribution of dielectric permittivity. If the measurement of the scattering field includes phase and amplitude, the values for $S_{ij}$ will be complex. Thus, measuring both phase and amplitude of the scattering field yields both real and imaginary parts of dielectric profile. In addition, if the incident field is polarized, measuring the vector scattering field will yield the dielectric permittivity corresponding to each direction of the applied field. In other words, eq. 19 provides images of anisotropic dielectric permittivities. Note that, if vector quantity is measured, then each element of the matrices, G, $G_o$, and S, is itself a 3×3 matrix, and each element of the column vectors $f_o^{(i)}$ and $f^{(s)}$, is itself a 3-dimensional vector.

Figure 1A:
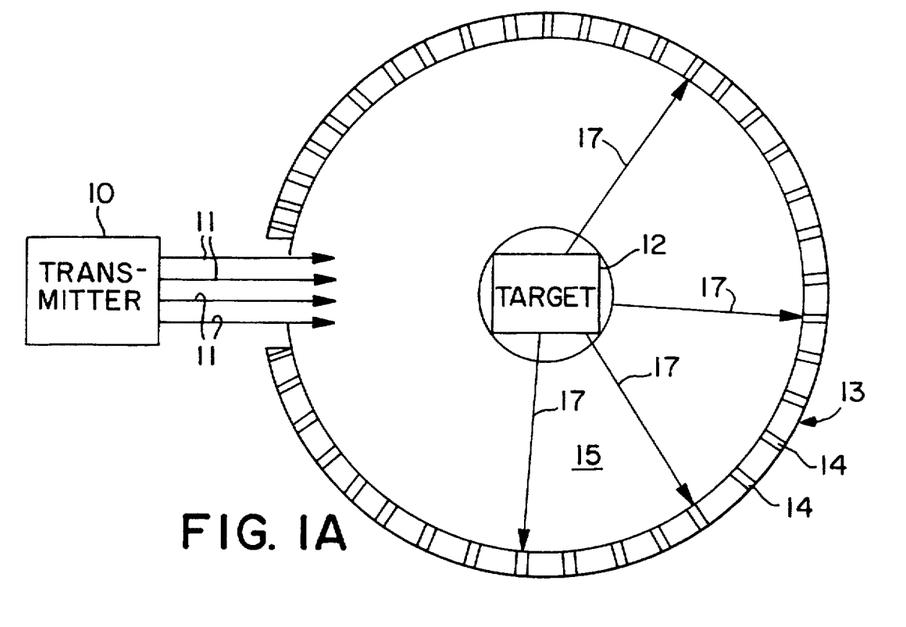
FIG. 1 is a block diagram of the microwave imaging system of the present invention.
Figure 1B:
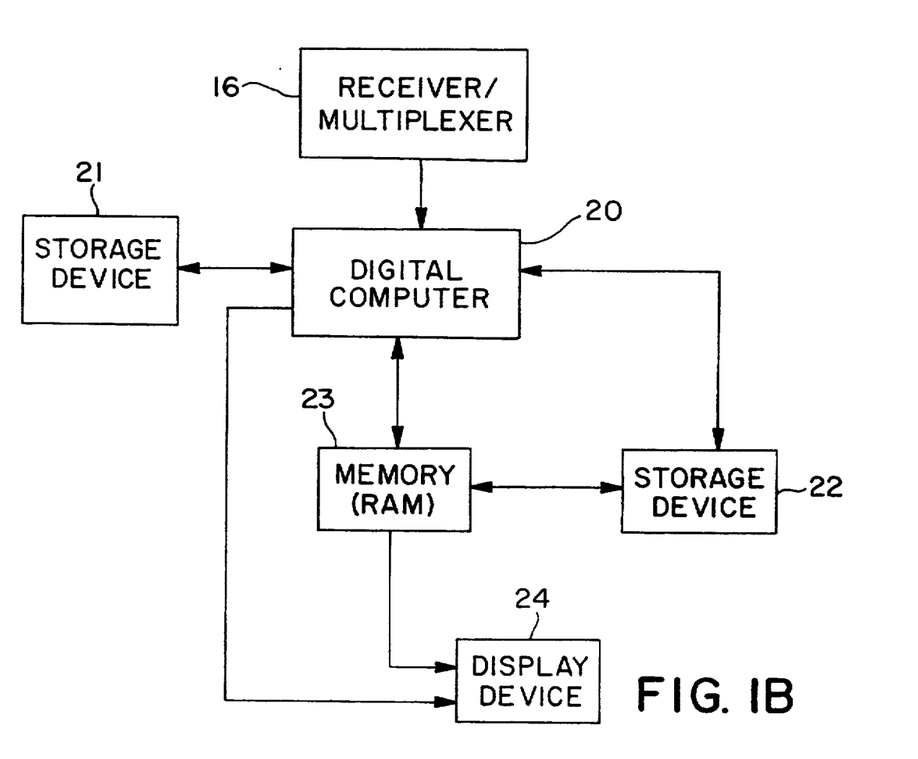

Referring now to FIG. 1, a block diagram illustrates the first embodiment of the microwave imaging system of the present invention. The imaging system includes a transmitter 10 which is generally composed of a microwave generator and a transmitting antenna. The transmitter 10 transmits microwaves 11 that are directed toward a target 12. The target 12 is surrounded by a receiving antenna 13 which preferably includes a plurality of coaxial cables 14. Disposed between the target 12 and the receiving antenna 13 is fluid filled chamber 15 which can expand or contract depending upon the configuration of the target 12. Scattering waves 17 are scattered from the target 12, pass through the water filled chamber 15 and are received by coaxial cables 14.

The coaxial cables are coupled to a data acquisition system including receiver/multiplexer 16 and suitable filtering circuits which convert the received signals into a digital format suitable for application to a digital computer 20. The digital computer 20 is coupled to first and second storage devices 21 and 22. The computer 20 also incudes a volatile memory 23 comprised of RAM integrated circuits. A display device 24, such as a CRT, is coupled to the computer 20. Examples of prior art data acquisition systems which could be adapted for use with the present invention are described in "Medical Applications of Microwave Imaging" by L. E. Larsen and J. H. Jacobi, IEEE Press, 1986, pgs. 126–129 and 143–144.

The display device 24 may be controlled by the digital computer 20 or may be independent of the digital computer 20. If the display 24 is controlled by the computer 20, it is connected to the computer 20 in a generally conventional fashion and used to display the data representing the three dimensional profile stored in the storage device 22. The data in storage device 22, however, may be downloaded to a convenient format such as a diskette and displayed in an independent or remote display device not controlled by the computer 20. In many instances only a selected portion or a two dimensional "slice" of the three dimensional profile would be displayed on the display 24.

Figure 2:
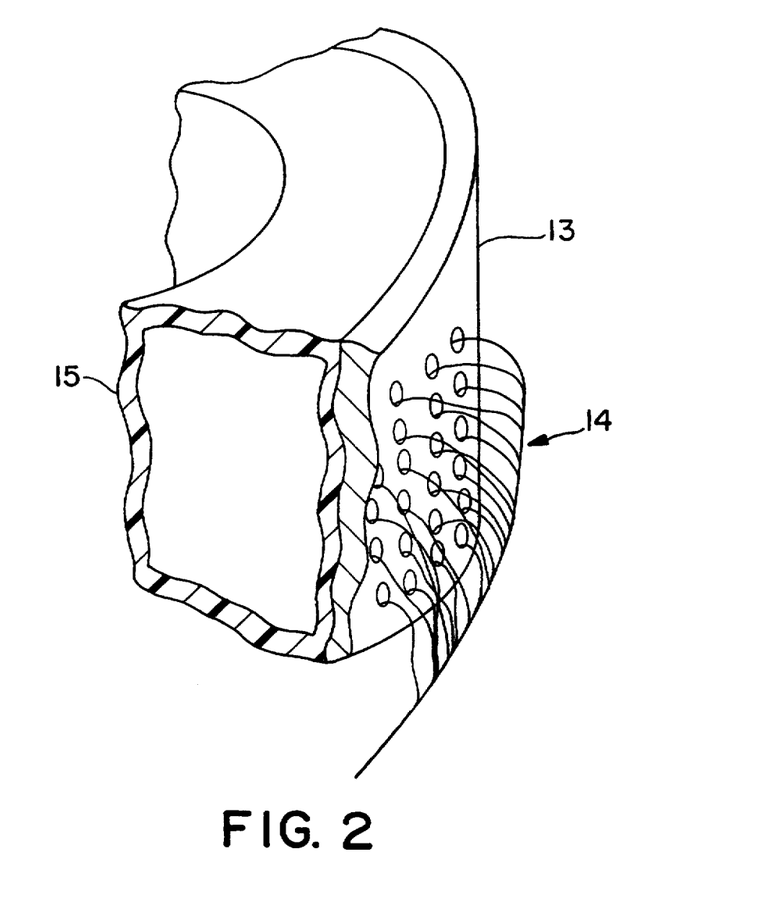
FIG. 2 is a partial isometric view of an antenna for use with the imaging system of FIG. 1.

Referring now to FIG. 2, a partial isometric view of the receiving antenna 13 is provided. The receiving antenna 13 is generally circular in shape and includes a plurality of coaxial cables 14 disposed in predetermined locations along the outer periphery of the antenna 13. The fluid filled chamber 15 is disposed between the receiving antenna 13 and the target 12.

In order to provide impedance matching for maximum penetration of microwaves into the liquid flow, the chamber 15 is filled with liquid having similar dielectric permittivity as that of the target 12. In medical applications, the fluid is typically water. The transmitting antenna of transmitter 10 is fixed in position with a design that provides a near-planewave beam pattern. The receiver antenna 13 is preferably a two-dimensional cylindrical array encompassing most of the target 12.

As the resolution is limited by the number of scattering waves 17 or data, it is desirable to pack a large number of antenna elements or coaxial cables 14 in the receiving array 13. This means that a large array is needed. On the other hand, in order to stabilize scattering inversion and achieve maximum three-dimensional resolution, it is desirable to place the receiving array 13 within a few wavelengths from the target. An initial microwave frequency of 0.5–1 GHz can be used. Another approach to increase the scattering data is to use a rotating array design, in which the array is rotated around the target 12 by a fraction of the interelement spacing for each snap shot of scattering data; e.g., rotating the array once by half of the interelement spacing provides twice as much data as the total number of array elements.

The scattered microwaves 17 are directly coupled to a number of waveguide-to-coaxial adapter feed elements 14 affixed to a plate in an array format. Each element 14 is connected to a data acquisition interface such as the receiver/multiplexer 16 via the waveguides or coaxial cables 14. This design provides higher quality image by eliminating nonlinear coupling of intermediate stage. The cross section of each element 14 is of the order of a few millimeters.

Equation 19 shows that, to construct the dielectric profile, $S_{ii}$, one needs to know the locations of the receiving antenna elements 14 and the target cells, $x_j$ and $y_i$, respectively, the incident fields $f_o^{(i)}(y_i)$, the measured scattered fields $f^{(s)}(X_j)$, and the matrices $G_o$ and $G^{-1}$., the matrix elements of $G_o$ and G are given by eqs.

15-17, from which $G^{-1}$ may be computed. It should be noted that the matrix elements of $G_o$ and G depend only on the background medium, the microwave frequency, the target cell size, and the relative space vectors between each target cell and each receiving element. Therefore, besides the scattering fields, all quantities needed to reconstruct the dielectric image are determined during the system design. Thus, once the microwave frequency and the geometry of the microwave antenna 13 are defined, the matrices for scattering inversion may be computed and become a permanent part of the system. Preferably, this data can be stored on diskettes and read by the storage device 21. To this end, one first determines a target region, which is the region occupied by the target 12. Then one measures the space vectors from the center of each cell to each receiving antenna site 14, a space vector is recorded for each pair of target cell and antenna site. All matrices needed for image reconstruction are determined by the collection of such space vectors and the microwave frequency. During the design phase, one may try various geometric configuration of the target cells and antenna sites to obtain optimal imaging quality and inversion stability. The advantage of this approach is that, once the matrices and their inversions are determined, they may be stored in the first storage device 21 and become a permanent part of the system. One may also construct a number of scattering sets, each corresponds to a desired resolution.

The major factor that determines the image resolution is the spatial sampling rate of the scatterer, which, in turn, is determined by the stability of inversion of G matrix. If the matrix is near singular, the inversion will be very sensitive to noise in the measured data. The stability of a matrix can be increased by de-symmetrizing the geometry of sampling of the scatterer space and scattering space. The so-called "condition numbers," which provide some measures of the stability of matrix inversion; the smaller is the condition number, the more stable is the inverse of the matrix. It turns out that, while keeping the scatterer $V_o$ fixed, rotating the scattering space, V, by a few degrees reduces the condition number for $10^{11}$ to $10^3$.

The acceptable magnitude of condition numbers is determined by making a model of a dielectric body with certain distribution of complex dielectric permittivity, and to calculate the scattering fields. The calculated fields are then employed as measured data to reconstruct the image, which may then be compared with the original model. From eqs. 7 and 8, one easily derives the following formula for scattering fields:

$$|f^{(s)}\rangle = G(S^{-1} - G_o)^{-1}|f_o^{(i)}\rangle \tag{20}$$

which provides the scattering field anywhere, in terms of the incident field inside the scatterer. In the case where the matrices G, $G_o$, and S have a dimension of 12, it has been found that a condition number of $10^4$ produces an image with dielectric permittivities in all cells equal to, up to the 6th decimal place, those of the original scatterer model. It appears that the upper limit of the condition number is about the inverse of the compute precision, viz., the smallest number recognized by the computer. For Green's matrices with condition number beyond the computer precision, we shall handle the inversion by a least-mean-square and singular value decomposition approach.

Another factor that may affect the stability is the dissipation of the background medium. In deriving the scattering matrix, as well as the inverse scattering formula, it is necessary to introduce damping in the background medium. This suggests that dissipation may play some role in disengaging the correlation between fields at different points. For this purpose, a water-immersed system such as chamber 15 is used. Besides the possibility of improving stability, a water-immersed system also has the advantage of eliminating undesired scattering and, for biological target, improving impedance matching at the target surface, thereby increasing the penetration depth of the probing microwave.

The third approach to stability is by least-mean-square and singular value decomposition (SVD), which is used to handle the case where the condition number of the Green's matrix is beyond the computer precision. In essence, this approach calls for more data than unknowns, viz., more measuring points than the number of cells in the target, then uses a least-mean-square method to determine the inverse solution. Eigen values of the scattering matrix that are smaller than the computer precision limit are discarded in the inverting process.

The second embodiment of the present invention provides a three dimensional microwave image using a Fourier transformation algorithm. The relationship of Fourier mapping is the principle of focusing of many types of waves, such as microwave focusing by phased array antennas, light wave focusing by optical lenses; focusing of acoustic waves and electron waves are also based on the same principle. The relationship may be used to construct an image of a scatterer. To achieve quantitative three-dimensional dielectric imaging, the first step is to quantify the Fourier mapping relationship between the vector scattering field in the Fräunhoffer zone and the excess dielectric permittivity of the target with respect to the background medium. However, the mapping between the scattering field and the scatterer's Fourier space is a two-dimensional one; the information on the third dimension is lost due to the far-field approximation. This is manifested by the fact that only the angular dependency of the scattering field contains information of the scatterer; the radial dependency of the scattering field is the trivial factor, $\exp(ikr)/r$. One approach to retrieve information of the third dimension is to include scattering data in the near zone where the radial dependency of the scattering field strongly depends on the scatterer, but then the relationship between source and scattering field will not be simply a Fourier transformation. Another approach to retrieve information of the third dimension is by scanning some parameters in addition to the scattering angle. Three scanning techniques may be considered, each gives a mapping between the scattering field and the target's Fourier space in mutually exclusive dimensions. Combining any pair of these three techniques will then provide information of all three dimensions of the target's Fourier space. Three-dimensional dielectric profile of the target may then be constructed by inverse Fourier transformation. The first scanning parameter is the scattering angle which maps the scattering field onto a spherical surface of the target's Fourier space, passing through its origin ($k=0$) and with the radius being the wave number, $k_m$, of the incident wave in the background medium. This is the mapping of the conventional scanning array antenna. The second scanning is to scan the frequency of the incident wave, which maps the scattering field to a line in the target's Fourier space. For backward ($v=\pi$) scattering field, the mapping yields a straight line radiating from the origin of the target's Fourier space, and stretching to the maximum value of $2 \cdot k_m$. The third scanning method is to scan the incident angle, which maps the backward scattering field onto a spherical surface in the target's Fourier space, centered at its origin and with radius being $2 \cdot k_m$. Though any pair of the three scanning methods suffice to retrieve information of all three dimensions, some combination of all three methods may optimize image resolution and minimize software and hardware requirements.

Referring back to FIG. 1, consider target 12 to be an arbitrary dielectric body, which will be the scattering object, occupying a region $V_o$ in a homogeneous background medium. Let $\epsilon_m$ and $\epsilon(X)$ denote, respectively, the dielectric permittivity of the background medium and that inside $V_o$. Thus the quantity $\epsilon(X) - \epsilon_m$ is localized in the sense that it vanishes outside $V_o$. Since the chamber 15 is filled with microwave absorbing material, the system may be treated as an open system without boundary. Consider now a plane wave incident upon the target. From the Maxwell's equations, one may derive the following expression for the scattering field:

$$E^{(s)}(x) = -\frac{1}{4\pi} \int\int\int [\nabla\nabla \cdot + k_m^2 \cdot I] \frac{\exp(ik_m|x-x'|)}{|x-x'|} \cdot \quad (21)$$

$$S(x')E(x')dx'$$

where $S(x)$ is the negative of the fractional excess dielectric permittivity of the target with respect to the background medium:

$$S(x) = -\frac{1}{\epsilon_m} [\epsilon(x) - \epsilon_m] \cdot I \quad (22)$$

and $E = E^{(i)} + E^{(s)}$ is the total field, with the incident field being a plane wave propogating with wave vector $k_m$:

$$E^{(i)}(x') = E_o \exp(ik_m \cdot x') \quad (23)$$

In order to rewrite eq. 1 into a Fourier transformation format, we shall assume the following conditions on the environment under which the scattering field is measured:

Small wavelength: $1/\text{Re}(k_m) << r$ (24)

Far-field: $r >> d$ (25)

Fräunhoffer diffraction: $1/\text{Re}(k_m) \geq d^2/r$ (26)

First-order scattering: $E(x') \approx E^{(i)}(x')$ for all $x' \in V_o$ (27)

where $k_m = 2\pi/\lambda_m$ is the wave number the microwave in the background medium, r the distance from the center of the target to the point of measurement, and d the width of the target. The first three conditions can be met by suitable system design. The last condition is valid only when the scatterer is not a strong scatterer, viz., if $S(x)$ is not too large. For a strong scatterer, second order term must be included in the imaging algorithm, to which we have developed some approach. With the above four conditions, eq. 1 may be rewritten as:

$$E^{(s)}(x) = -\frac{k_m^2}{4\pi} \frac{\exp(ik_m r)}{r} (\overleftrightarrow{I} - \hat{x}\hat{x}) \cdot \quad (28)$$

$$E_o \int\int\int S(x') \exp[-i(k_m\hat{x} - k_m) \cdot x'] dx'$$

The right hand side of the above equation is, indeed, the Fourier transform of $S(x)$:

$$E^{(s)}(x) = -\frac{\sqrt{(2\pi)}}{2} \frac{\exp(ik_m r)}{r} k_m^2 (\overleftrightarrow{I} - \hat{x}\hat{x}) \cdot E_o \widetilde{S}(k_m\hat{x} - k_m) \quad (29)$$

where $S(x)$ and $\widetilde{S}(k)$ are the Fourier pair as defined by:

$$S(x) = \frac{1}{(2\pi)^{3/2}} \int\int\int \widetilde{S}(k) e^{ik \cdot x} dk \quad (30)$$

$$\widetilde{S}(k) = \frac{1}{(2\pi)^{3/2}} \int\int\int S(x) e^{-ik \cdot x} dx$$

Equation 29 shows that the Fräunhoffer scattering field in the direction $\hat{x}$ is mapped to $\widetilde{S}$ at $k = k_m\hat{x} - k_m$. Conversely, the value of $\widetilde{S}$ at $k = -2k_m \cdot \hat{k}\hat{k}$ may be obtained by measuring the scattering field in the direction $\hat{x} = \hat{k}_m - 2\hat{k}_m \cdot \hat{k}\hat{k}$. Therefore, eq. 9 gives $$\widetilde{S}(-2k_m \cdot \hat{k}\hat{k}) = -\frac{2}{\sqrt{(2\pi)}} \frac{r}{k_m^2} \exp(-ik_m r) \frac{1}{E_{o\perp} \cdot E_{o\perp}} E_o \cdot \quad (31)$$

$$E^{(s)}(r\hat{k}_m - 2r\hat{k}_m \cdot \hat{k}\hat{k})$$

where $E_{o\perp}$ is the component of the incident field in the direction perpendicular to x.

Figure 3:
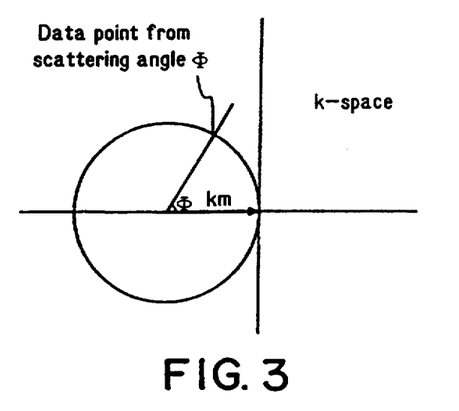
FIGS. 3 to 8 are diagrams useful in explaining the second embodiment of the present invention.

Equation 29 shows that the scattered field in the Fräunhoffer zone is proportional to the Fourier transform, $\widetilde{S}(k)$, of the fractional excess dielectric permittivity of the target, $S(x')$. However, scattering measurement throughout the space does not provide sufficient data for inverse Fourier transformation. First of all, radial dependence of Fräunhoffer field is the trivial $e^{ikr}/r$ factor, which does not contain target information. Therefore, the scattered field provides only a two-dimensional information for $\widetilde{S}(k)$. Secondly, due to the term $-k_m$ in the argument of $\widetilde{S}$ in the right hand side of eq. 29, the scattered field provides only information on $\widetilde{S}(k)$ for only values of k which are against the incident direction $\hat{k}_m$. Indeed, for a non-dissipative background medium, measurement of all the Fränhoffer scattered fields provides values of $\widetilde{S}(k)$ on the surface of a sphere of radius $k_m$ centered at $k = -k_m$. FIG. 3 shows such sphere from the incident wave $\exp(ik_m \cdot x)$.

Figure 4:
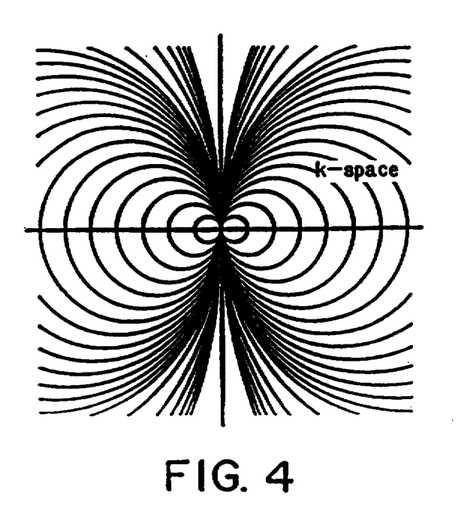
Figure 5:
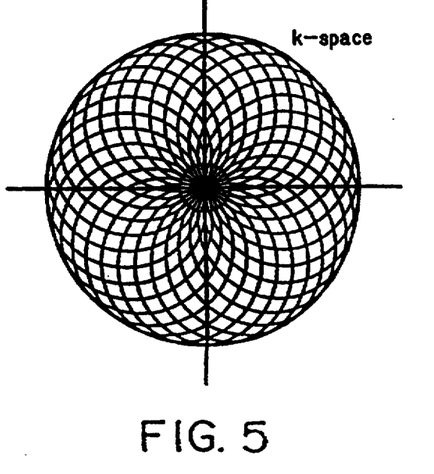
Figure 6:
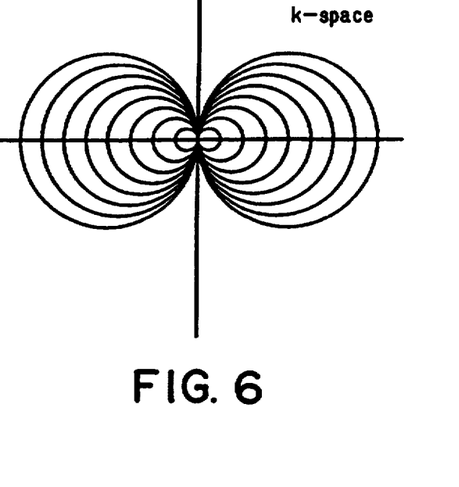
Figure 7:
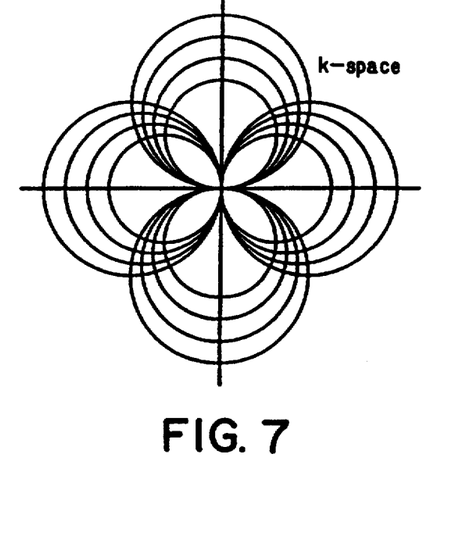

There are two approaches to obtain three-dimensional data in the Fourier space of $\widetilde{S}(k)$. The first step is by sweeping the frequency of the incident wave, thereby scanning the radius of the sphere shown in FIG. 3. Since scattering data provide only $S(k)$ for k against the incident direction, scattering measurement from two opposite incident directions are needed. FIG. 4 illustrates the data in the k-space provided by frequency sweeping and two opposite incident directions. Instead of sweeping the frequency, the second approach obtains three-dimensional data by scanning the incident direction. This is illustrated in FIG. 5. The first approach has simpler hardware configuration, whereas the second has the advantage of ridding the problem of dielectric relaxation, since only one frequency is used. Some combination of these two approaches may offer optimal result. As the resolution is proportional to the total bandwidth, which is the sum of the bandwidths of all incident directions, reducing frequency sweeping range by a factor of two may be compensated by doubling incident directions. This is illustrated in FIG. 6 and FIG. 7; The surfaces in FIG. 6 represent the collection of data points of $\bar{S}(k)$ obtained from eight frequency samples coupled with a pair of opposite incident directions, while the surfaces in FIG. 7 represents those obtained from four frequency samples and four incident directions. Indeed, the latter provides more uniform data distribution in k-space.

Figure 8:
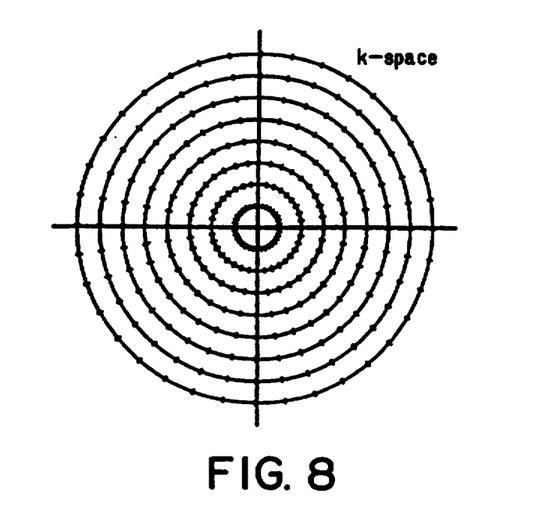

By studying the geometry of the spheres in the k-space, many other approaches can be devised from various combinations of frequency sweeping, incident direction scanning, and scattering angle scanning. For example, three-dimensional imaging may be achieved by measuring only backward scattering field, together with frequency sweeping and incident direction scanning. The backward scattering field corresponds to, in the k-space, the point of the sphere at the other end of the diameter opposite to the origin. The result is similar to that shown in FIG. 5, except that, for each sphere, only the point corresponding to the backward scattering is used. FIG. 8 illustrates the set of data points from backward scattering measurement with eight frequency samples and thirty-six scattering angles.

From FIG. 4 and FIG. 5, one sees that three-dimensional information on the Fourier transform of the fractional excess dielectric permittivity with respect to the background medium, S(x), may be obtained by either scanning the frequency of the probing microwave, or by scanning the direction of the incident wave. As illustrated in FIG. 6 and FIG. 7, three-dimensional imaging may also be obtained by a combination of both methods. For each frequency and each incident direction, scattering field will be measured at a set of scattering angles, representing a set of points on the corresponding the spherical surface in the k-space of $\bar{S}(k)$. It is desirable to determine an optimal combination of frequency sweeping and incident direction scanning, and to make a suitable selection of scattering angles.

From the computation aspect, inverse Fourier transform is best carried out by a Fast Fourier Transform (FFT) routine. Currently, FFT routines are readily available in cartesian coordinates. On the other hand, from the above figures, one sees that the data points from scattering measurement are the intersections of the spherical surfaces, such as those shown in FIG. 7, and the rays from the center of each sphere to each direction of the scattering angles, which depend on the placement of the measuring antenna and its elements. These intersection points do not fall on the lattice points of a rectangular lattice, therefore, some interpolation routine, such as the cubic spline routine must be employed to calculate the scattering field at the rectangular lattice points. Furthermore, it can be appreciated from FIG. 6 and FIG. 7, the data points in k-space are rather unevenly distributed, especially for the case where only two opposite incident directions are employed. Therefore, the quality of images depends on the geometrical arrangement of the spheres and the rays. An evenly distributed data points will provide better imaging quality and requires less computation time. However, from the hardware point of view, it is must easier, and less expensive to design a system with less incident directions. Comparison of FIG. 4 through FIG. 7 indicates that a system with two pairs of opposite incident directions (FIG. 7) may be the best compromise.

The system used to obtain and process data is essentially the same as illustrated in the block diagram of FIG. 1. The one significant hardware difference associated with the second embodiment is that the receiving antenna 13 may be disposed at a greater distance from the target 12 than in the first embodiment of the present invention. The other major differences are that the general purpose computer 20 is programmed to solve the Fourier transform algorithms described above, and that the storage device 21 stores an interpolation matrix (or matrices) to map the measured scattering data to interpolated data on a rectangular lattie points. The data generated from the Fourier transform algorithms is a three dimensional profile of the dielectric permittivity of the target 12. The data representing a three dimensional profile can be stored in storage device 22 and displayed on a suitable device 24.

The transmitting antenna of transmitter 10 may be a horn antenna or an array antenna with a specification that provides a near-planewave beam pattern. The following three transmitting configurations may be considered:

1) Frequency Sweeping Configuration: The transmitting antenna is fixed in position and frequency sweeping over a selected bandwidth of, 0.1-10 GHz.
2) Incident Direction Scanning Configuration: The frequency is fixed at, 10 GHz, and each receiving array element is a bidirectional antenna. For each transmission, a small subarray serves as the transmitting antenna and the rest takes scattering data. An array multiplexer will scan the transmitting subset over the entire receiving array so as to provide scanning of incident directions. A phase and amplitude conjugation will be applied to the transmitting subarray so as to create a near-plane wave.
3) Mixed Configuration: A number of transmitting antennas are employed to provide, 8, incident directions, together with frequency sweeping over a selected bandwidth. The multiple incident directions may also be achieved by a single movable transmitting antenna which is rotated to a number of positions.

A water-buffered configuration using a relatively small water bag provides the following advantages:

1) With a permittivity as high as 74 at 37° C. for 1-3 GHz microwaves, water contracts the wavelength by a factor of 8.6, thereby increases image resolution by the same factor; smaller wavelength also reduces interference between antenna elements and allows the more receiving elements to be packed on the chamber surface.
2) A background medium of water reduces the fractional variation of dielectric permittivity, thereby makes the most biological targets weak microwave scatters, which improves the precision of the approximation made in deriving the Fourier mapping relationship.
3) Impedance matching the biological target maximizes microwave penetration.

However, the water-buffered design requires that the receiving array 13 be in contact with the water bag, thus scattering data are taken at relatively close range, which lessen the accuracy of the Fräunhoffer approximation. One approach to solve the problem is to use a relatively large water-filled chamber 15. A compromised approach is to use air as background medium with frequency sweeping over a wider bandwidth. For a system with bandwidth greater than 30 GHz, some parameterization of dielectric relaxation may be needed to compensate the additional unknown quantities.

While the invention has been described in its preferred embodiments, it is to be understood that the words that have been used are words of description rather of limitation, and that changes within the purview of the present claims may be made without departing from the true scope of the spirit of the invention in its broader aspects.

We claim:

1. A three dimensional quantitative dielectric imaging system comprising:
   a transmitter for transmitting microwaves toward a target;
   a receiver having an antenna disposed to receive waves scattered by the target in order to obtain a first set of scatter data in the form of a vector;
   a processor for processing the first set of scatter data in order to generate a three dimensional profile of the dielectric permittivity of the target, wherein said processor uses an image reconstruction algorithm which utilizes predetermined matrices to operate on at least said first set of scatter data without inverting a matrix formed from said scatter data; and
   an output device for displaying a selected amount of the three dimensional profile generated by the processor.

2. A three dimensional quantitative dielectric imaging system according to claim 1 wherein said processor processes the scatter data in accordance with an image reconstruction algorithm defined by the equation:

$$S_{ii} = \frac{-1}{\epsilon_m} [\epsilon(y_i) - \epsilon_m] = \frac{\sum_j (G^{-1})_{ij} f^{(s)}(x_j)}{f_o^{(s)}(y_i) + \sum_{j,k} (G_o)_{ij}(G^{-1})_{jk} f^{(s)}(x_k)}.$$

3. A quantitative dielectric imaging system according to claim 1, which includes a fluid containing means disposed between the target and the antenna of said receiver.

4. A quantitative dielectric imaging system according to claim 1, wherein the antenna includes an array disposed around the target.

5. A quantitative dielectric imaging system according to claim 4, wherein said antenna array includes a plurality of waveguides disposed in predetermined locations in said array.

6. A three dimensional quantitative dielectric imaging system comprising:
   a transmitter for transmitting microwaves toward a target;
   a receiver having an antenna disposed to receive waves scattered by the target in order to obtain scatter data;
   a processor for processing the scatter data in order to generate a three dimensional profile of the dielectric permittivity of the target, wherein said processor uses a Fourier transform algorithm to generate the three dimensional profile; and
   an output device for displaying a selected amount of the three dimensional profile generated by the processor.

7. A quantitative dielectric imaging system according to claim 6, which includes a fluid containing means disposed between the target and the antenna of the receiver.

8. A quantitative dielectric imaging system according to claim 6, wherein the antenna includes an array disposed around the target.

9. A quantitative dielectric imaging system according to claim 8, wherein said antenna array includes a plurality of waveguides disposed in predetermined locations in said array.

10. A method of quantitative dielectric imaging, comprising the steps of:
    transmitting microwaves from a transmitter toward a target;
    receiving the microwaves scattered by the target with an antenna of a receiver;
    converting the scattered microwaves into a first set of scatter data in the form of a vector;
    processing the first set of scatter data to generate a three dimensional profile of the dielectric permittivity of the target in accordance with an image reconstruction algorithm which utilizes predetermined matrices to operate on at least the first set of scatter data without inverting a matrix formed from said scatter data; and
    displaying a selected amount of the three dimensional profile on an output device.

11. A method according to claim 10 which further includes the step of generating matrices, and inverting any of said matrices prior to transmitting the microwaves for use by the processor for image reconstruction during an imaging operation.

12. A method according to claim 11 which further includes the step of stabilizing the inverted scattering matrix.

13. A method according to claim 11 wherein said scattering matrices are computed prior to transmitting microwaves toward the target and the computed scattering matrices are stored in a storage device.

14. A method of quantitative dielectric imaging, comprising the steps of:
    transmitting microwaves from a transmitter toward a target;
    receiving the microwaves scattered by the target with the antenna of a receiver;
    converting the scattered microwaves into scatter data with the receiver;
    processing the scatter data in a processor in order to generate a three dimensional profile of the dielectric permittivity of the target, wherein the processing of the scatter data includes a mapping of a scattering field and the fourier space of the target in mutually exclusive dimensions; and
    displaying a selected amount of the three dimensional profile on an output device.

15. A method according to claim 14, wherein the antenna includes an array placed anywhere outside the target, at a distance relatively near to relatively far from the target.

* * * * *

UNITED STATES PATENT AND TRADEMARK OFFICE
CERTIFICATE OF CORRECTION

PATENT NO. : 5,363,050

DATED : November 8, 1994

INVENTOR(S) : GUO et al.

It is certified that error appears in the above-indentified patent and that said Letters Patent is hereby corrected as shown below:

Column 17, line 21, change "waves" to --microwaves--;

Column 17, between lines 23 and 24, insert as a new paragraph -- a storage device which stores system matrices and their inversions which are needed for image reconstruction; --;

Column 17, lines 25-31, delete in its entirety and replace with -- in accordance with an image reconstruction algorithm wherein said processor utilizes the system matrices and their inversions to operate on at least said first set of scatter data without inverting a matrix formed from the scatter data in order to generate a three dimensional profile of the dielectric permittivity of the target; and --;

Column 17, line 61, change "receiver" to --receiving device--;

Column 17, line 61, after "antenna" insert --array--;

Column 17, delete lines 62-66 in its entirety and replace with -- microwaves scattered by the target and including a multiplexer which scans at least one of the following two parameters, the incident direction and the frequency of the transmitted microwave, and which scans the antenna array and selects at least two of the following types of scatter data: 1) data indicative of respective scattering angles of the scattered waves, 2) data indicative of respective incident angles of the transmitted microwaves and 3) data indicative of the frequency of the transmitted microwaves;

a processor for processing the scatter data, wherein said processor performs an inverse Fourier transformation on the scatter data and generates a three dimensional profile of the dielectric permittivity of the target; and --;

Column 18, deletes lines 1 and 2;

Column 18, line 3, change "of" to --to--;

Column 18, lines 28 and 29, change "predetermined" to --system--;

Column 18, line 35, change "matrices" to --the system matrices--;

UNITED STATES PATENT AND TRADEMARK OFFICE
CERTIFICATE OF CORRECTION

PATENT NO. : 5,363,050  
DATED : November 8, 1994  
INVENTOR(S) : GUO et al.

Page 2 of 2

It is certified that error appears in the above-indentified patent and that said Letters Patent is hereby corrected as shown below:

Column 18, line 36, change "said" to --the system--;
Column 18, lines 40 and 41, change "scattering matrix" to --system matrices--
Column 18, lines 42 and 43, change "said scattering" to --the system--;
Column 18, lines 44 and 45, change "scattering" to --system--.

Signed and Sealed this

Sixteenth Day of May, 1995

Attest:

BRUCE LEHMAN

*Attesting Officer*  *Commissioner of Patents and Trademarks*